(12) United States Patent
Gorczynski

(10) Patent No.: US 7,196,243 B2
(45) Date of Patent: Mar. 27, 2007

(54) TRANSGENIC ANIMAL CONTAINING CD200 AND USES THEREFOR

(75) Inventor: Reginald M. Gorczynski, Willowdale (CA)

(73) Assignee: Trillium Therapeutics Inc., Toronto (CA)

( * ) Notice: Subject to any disclaimer, the term of this patent is extended or adjusted under 35 U.S.C. 154(b) by 579 days.

(21) Appl. No.: 10/406,004

(22) Filed: Apr. 3, 2003

(65) Prior Publication Data

US 2003/0237106 A1    Dec. 25, 2003

Related U.S. Application Data

(60) Provisional application No. 60/369,335, filed on Apr. 3, 2002.

(51) Int. Cl.
*A01K 67/027* (2006.01)
*A01K 67/00* (2006.01)
*G01N 33/00* (2006.01)
*C12N 15/00* (2006.01)
*C12P 21/06* (2006.01)
*C12N 5/00* (2006.01)

(52) U.S. Cl. ................... 800/18; 800/3; 800/8; 800/14; 800/21; 800/24; 800/25; 435/69.1; 435/320.1; 435/325; 435/455

(58) Field of Classification Search ................... None
See application file for complete search history.

(56) References Cited

U.S. PATENT DOCUMENTS

| 5,168,062 A | 12/1992 | Stinski |
| 5,385,839 A | 1/1995 | Stinski |
| 6,749,854 B2 | 6/2004 | Gorczynski et al. |

OTHER PUBLICATIONS

Barclay et al, 2002, Trends in immunology 23:285-290.*
Gavin et al, 2003, J Immunol. 171: 3034-3046, Abstract).*
Bockamp et al. Physiol. Genomics 11:115-132, 2001.*
Bishop Reproductive Nutrition and Development 36: 607-616, 1996.*
Rulicke and Hubischer, Experimental Physiology 85: 589-601.*
Holschneider et al. Int J. Devl. Neuroscience 18:615-618, 2001.*
Hoek et al., Down-Regulation of the Macrophage Lineage Through Interaction with OX2 (CD200), Science, vol. 290, pp. 1768-1771, 2000.

* cited by examiner

*Primary Examiner*—Sumesh Kaushal
*Assistant Examiner*—Kelaginamane T. Hiriyanna
(74) *Attorney, Agent, or Firm*—Bereskin & Parr; Micheline Gravelle

(57) ABSTRACT

The present invention is directed toward a transgenic non-human animal and uses thereof, wherein each of the cells of the animal contain a transgene comprising a nucleic acid sequence encoding CD200.

9 Claims, 6 Drawing Sheets

TRANSGENIC ANIMAL CONTAINING CD200 AND USES THEREFOR

This application claims the benefit under 35 USC §119(e) of U.S. provisional application Ser. No. 60/369,335 filed Apr. 3, 2002 which is incorporated herein by reference.

FIELD OF THE INVENTION

The invention relates to transgenic non-human animals which express CD200 and uses thereof.

BACKGROUND OF THE INVENTION

Intense interest has centred on the need for development of novel immunosuppressant agents and/or regimens which might have clinical utility in disorders including autoimmunity, allergy and transplantation (1). Given the evidence that efficient induction of T cell immunity depends upon the existence of accessory signals provided by a variety of costimulatory molecules (and their natural ligands) (2–6) it had been hoped that systematic blockade of such costimulation might provide the immunosuppression required. In general however, results of trial, both in experimental animals and man, on the use of these reagents alone, or even in combination, have not provided evidence for consistent inhibition of immunity (7–9). More recent studies have begun to characterize receptor:ligand molecules which deliver regulatory (suppressive signals) directly to antigen activated T cells (10–14). Note that, at least for CTLA4, there is evidence that the same molecule may deliver either positive or negative costimulatory signals, according to the overall molecular milieu in which T cell activation occurs (15, 16).

The inventor has characterized another ligand:receptor pair, CD200:CD200R, which he has implicated in the direct delivery of suppressive responses after antigen challenge (14, 17). Treatment of animals with foreign allo- or xeno-grafts, or immunized with bovine collagen, with a soluble form of CD200 (CD200Fc) prevents graft rejection or development of collagen-induced arthritis (CIA) respectively (18). Similar effects are observed after infusion of a cross-linking anti-CD200R (19). Supporting evidence for a role for CD200:CD200R interactions in regulation of inflammation/autoimmunity comes from work of Hoek et al, who recently described some of the phenotypic properties of CD200 KO mice (20). These animals showed increased susceptibility to both CIA and experimental allergic encephalomyelitis, an animal model of multiple sclerosis, along with evidence for increased proliferation of CD200R+ cells. These data have suggested a physiological role for CD200 in the regulation of activation of CD200R+ cells of the monocyte/myeloid lineage, which are presumably in turn responsible for inflammation in these conditions. The inventor has also provided evidence for expression of CD200R on cells of T lymphocyte origin (17), and hypothesize that CD200 might exert a more direct role on T cell activation (22).

It would be useful to have an animal in which inducible overexpression of CD200 can be achieved in order to study the role of CD200 in various diseases.

SUMMARY OF THE INVENTION

A transgenic mouse (background) expressing a murine CD200 cDNA linked (at the C-terminal) to a green fluorescent protein tag (GFP) and under control of a tetracycline response element (TRE), was prepared. The transgenic CD200 mouse was mated with a commercial transgenic mouse carrying the reverse tetracycline regulated transactivator gene under control of a human cauliflower mosaic virus (CMV) promoter, to create an F1 hybrid expressing CD200 under positive control by exposure to doxycyline. Exposure of mice to doxycycline in the drinking water led to enhanced GFP expression in multiple organs and increased CD200 expression. Skin grafts from F1 mice were transplanted to allogeneic (C3H) recipients in the prescence/absence of re-exposure to doxycycline. In addition, lymphocyte cultures were initiated using F1 cells as responder or stimulator cells in allogeneic MLRs, again in the presence or absence of tetracycline. The data demonstrate that overexpression of CD200 in transgenic mice, or in skin grafts from these mice, leads to suppressed induction of allo-rejection responses, which has a clinical utility in transplantation. The non-human transgenic animals of the present invention are useful in studying CD200 and diseases wherein CD200 is implicated, including autoimmune disorders, graft rejection, fetal loss and tumor rejection. The animals may be used to develop potential diagnostic or therapeutic agents for such diseases.

The present invention is directed toward a transgenic non-human animal wherein each of the cells of the animal contain a transgene comprising a nucleic acid sequence encoding CD200. The present invention is further directed toward a cell containing a transgene comprising a nucleic acid sequence encoding CD200. The present invention is further directed toward a vector comprising a nucleic acid sequence encoding CD200.

The invention further relates to the use of the transgenic animal of the invention to study and design therapies for diseases involving CD200 such as graft rejection, fetal loss, tumor rejection and autoimmune disease.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

I. Transgenic Animal

Figure 1:
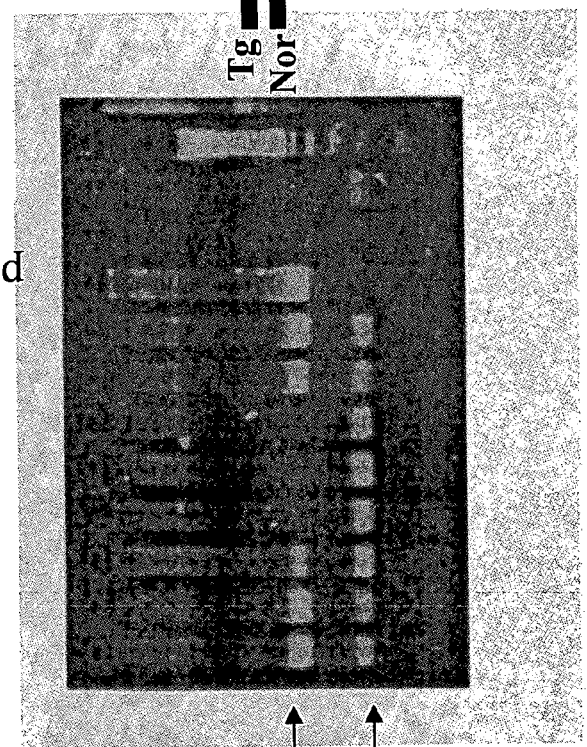
FIG. 1 is an analysis of transgenic expression of rtTA (panel a) and TRE-CD200-GFP (panel b) in mice backcrossed (2 generations) to C57BL/6. Expression of endogenous CD200 was detected using the same 5' primer and a 3' antisense primer from the 5' end of the intron immediately downstream of exon 3 (V-region exon of CD200). Housekeeping genes for rTA mice were prepared as per the breeder's instructions (Jackson Labs).
Figure 1:
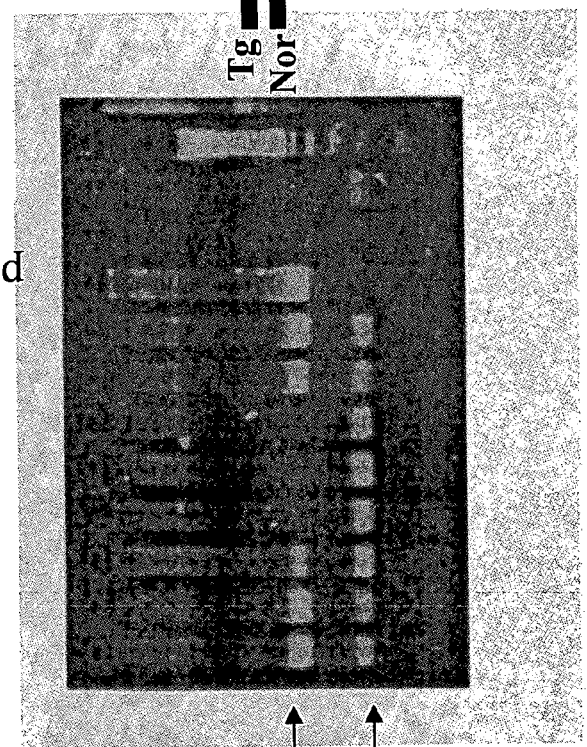

The present invention provides a transgenic non-human animal wherein each of the cells of the animal contain a transgene comprising a nucleic acid sequence encoding CD200.

The CD200 sequence can be from any animal. Preferably, the CD200 sequence is from the same species of animal being used to prepare the transgenic animal. For example, when preparing a transgenic mouse, murine CD200 is preferably used. The CD200 sequence may be obtained from known sources or obtained using screening techniques or DNA synthesis techniques. CD200 sequences can be obtained from Genbank. The human sequence of CD200 has accession no. M17226 X0523; the rat sequence no. X01785; and the mouse sequence of CD200 has accession no. AF029214. The nucleic acid sequence of CD200 can be any sequence that is sufficient to express the CD200 protein including genomic DNA and cDNA. The sequence can be modified as compared to the known sequence provided the modified sequence still encodes a functional CD200 protein.

The term "transgenic non-human animal" includes any member of the animal kingdom, except humans, in which one or more cells contain a transgene introduced by way of human intervention such as by transgenic techniques known in the art. The nucleic acid is introduced into the cell, directly or indirectly, by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. Non-limiting examples of animals that may be used in the present invention include mice, rats, squirrels, hamsters, guinea pigs, rabbits, pigs, sheep, baboons, monkeys, chimpanzees, birds and amphibians. Preferably, the animal is a mouse.

The term "transgene" as used herein refers to a construct for introducing CD200 to a non-human animal to prepare a transgenic non-human animal. The transgene may or may not be an integral part of a chromosome. If the transgene is integrated into a chromosome, it may or may not be located at the same site as its corresponding endogenous gene sequence. The transgene will be integrated into the genome of the animal so that the CD200 is capable of being expressed in all cells. The transgene will also contain the necessary regulatory sequences to allow for expression of the CD200 protein. By introducing the transgene, the transgenic animal will express CD200 in its cells at a level that is higher than non-transgenic or wild type animals.

The transgene will contain nucleotide sequences which contain transcriptional and translational regulatory information, and such sequences will be "operably linked" to nucleotide sequences which encode the CD200 protein. The term "linked" refers to in frame DNA regions, each encoding a protein or partial protein. An operable linkage is a linkage in which the regulatory nucleic acid sequences and the nucleic acid sequence encoding CD200 are connected in such a way as to permit CD200 expression. The regulatory regions needed for gene expression in general include a promoter region as well as the nucleic acid sequences which, when transcribed into RNA, will signal the initiation of protein synthesis.

The transgene of the invention preferably contains a promoter region and/or a transcriptional control region, which may be constitutive or inducible. The transcriptional control region may be composed of cis-acting elements which activate or repress transcription in response to binding of transacting factors. A promoter region and/or a transcriptional control region would be operably linked to a nucleic acid sequence if the promoter/control region were capable of effecting transcription of the nucleic acid sequence.

The "transcriptional control region" can include sequences which are naturally responsible for expressing CD200 or may include sequences of a different origin. In particular, the sequences can be sequences of eukaryotic or viral genes or derived sequences which stimulate or repress transcription of a gene in a specific or non-specific manner and in an inducible or non-inducible manner. The transcriptional control region can be derived from the genome of a virus, including the adenovirus used. In this regard, there may be mentioned, for example, the promoters of the E1A, MLP, CMV and RSV genes and the like. Alternatively, the transcriptional control region can be derived from ubiquitous genes including those encoding HPRT, vimentin, actin, tubulin, intermediate filaments including desmin, neurofilaments, keratin, GFAP, therapeutic genes (including MDRs, CFTR, factor VIII), tissue-specific genes such as actin, as well as from genes which are preferentially activated in dividing cells, or are expressed in response to stimuli such as the steroid hormone receptor, the retinoic acid receptor. Also useful as control regions are those that are regulated by tetracycline, and control regions associated with cytomegalovirus immediate-early genes, retroviral LTR, metallothionein, SV-40, E1a, the mouse mammary tumor virus (MMTV) steroid-inducible promoter, Moloney murine leukemia virus (MMLV) promoter and the promoter of the MLP gene. Tetracycline-regulated transcriptional modulators and CMV promoters are described in WO 96/01313, U.S. Pat. Nos. 5,168,062 and 5,385,839, the contents of which are incorporated herein by reference.

In one aspect, the present invention features a transgenic non-human animal containing in all cells a transgene comprising a nucleic acid sequence encoding CD200 which is operably linked to a transcriptional control region. The transcriptional control region can be any region that can regulate the expression of CD200. The transcriptional control region is preferably inducible rather than constitutive.

In a specific embodiment, the transgene of the invention includes a CD200 gene under the control of a tetracycline response element. The expression of the transgene may be regulated or induced by the addition of doxycyline in the drinking water of the non-human animal. Other promoter systems include the insulin promoter, where expression is under control of of insulin secretion; use of the native promoter (CD200) such that expression is regulated in a more physiological sense; and a number of other drug-induced promoters.

In another aspect, the present invention provides a transgenic non-human animal containing in all cells a transgene comprising a nucleic acid sequence encoding CD200 linked to a reporter gene.

A "reporter gene" refers to any gene for which gene expression can be monitored. The reporter can be any gene, including green fluorescent protein, chloramphenicol acetyltransferase, alkaline phosphatase, beta-glucuronidase or luciferase. Linking a reporter gene to CD200 (such as GFP) to prepare a fusion protein can be particularly useful for such screening methods since the aggregation can be monitored by fluoresence intensity. Other exemplary fusion polypeptides include other fluorescent proteins, or modifications thereof, glutathione S transferase (GST), maltose binding protein, poly His, and the like, or any type of epitope tag. Such fusion polypeptides can be detected, for example, using antibodies specific to the fusion polypeptides. The fusion polypeptides can be an entire polypeptide or a functional portion thereof so long as the functional portion retains desired properties, for example, antibody binding activity of fluorescence activity. Alternatively, antibodies specific for CD200 can be used to monitor a CD200 phenotype.

In yet another aspect, the present invention features a transgenic non-human animal containing in all cells a transgene comprising a nucleic acid sequence encoding CD200 linked to a reporter and operably linked to a transcriptional control region.

The present invention is further directed towards a transgenic mouse containing in all cells a transgene comprising a nucleic acid sequence CD200 of mouse origin. Preferably, the transgene comprises a murine CD200 sequence linked to a reporter. In a further aspect, the present invention features a transgenic mouse containing in all cells a transgene comprising a nucleic acid sequence CD200 of mouse origin operably linked to a transcriptional control region. In yet another aspect, the present invention features a transgenic mouse containing in all cells a transgene comprising a nucleic acid sequence encoding a nucleic acid sequence CD200 of mouse origin linked to a reporter and operably linked to a transcriptional control region.

The present invention is further directed towards a cell containing a transgene comprising a nucleic acid sequence encoding CD200. Preferably the cell is an embryonic stem cell. More preferably, the cell is an embryonic stem cell of mouse origin.

In one aspect, the present invention features a cell comprising a nucleic acid sequence encoding CD200 linked to a reporter. In a further aspect, the present invention features a transgene comprising a nucleic acid sequence encoding CD200 which is operably linked to a transcriptional control region. In yet another aspect, the present invention features a transgene comprising a nucleic acid sequence encoding CD200 linked to a reporter and operably linked to a transcriptional control region.

The present invention is further directed towards a cell containing a transgene comprising a nucleic acid sequence CD200 of mouse origin. The transgene preferably comprises a murine CD200 sequence linked to a reporter. In a further aspect, the present invention features a cell containing a transgene comprising a nucleic acid sequence CD200 of mouse origin operably linked to a transcriptional control origin. In yet another aspect, the present invention features a cell containing a transgene comprising a nucleic acid sequence encoding CD200 of mouse origin linked to a reporter and operably linked to a transcriptional control region.

The present invention is further directed towards a vector comprising a nucleic acid sequence encoding CD200. In one aspect, the present invention features a vector comprising a nucleic acid sequence encoding CD200 linked to a reporter. In a further aspect, the present invention features a vector comprising a nucleic acid sequence encoding CD200 which is operably linked to a transcriptional control region. In yet another aspect, the present invention features a vector comprising a nucleic acid sequence encoding CD200 which is linked to a reporter and operably linked to a transcriptional control region.

The present invention is further directed towards a vector comprising a nucleic acid sequence CD200 of mouse origin. In one aspect, the present invention features a vector comprising a nucleic acid sequence CD200 of mouse origin linked to a reporter. In a further aspect, the present invention features a vector comprising a nucleic acid sequence CD200 of mouse origin operably linked to a transcriptional control region. In yet another aspect, the present invention features a vector comprising a nucleic acid sequence CD200 of mouse origin linked to a reporter and operably linked to a transcriptional control region.

II. Preparation of Transgenic Animals

As mentioned previously, the present invention extends to all non-human animals that can be rendered transgenic by inserting a transgene containing a nucleic acid molecule encoding CD200. To produce transgenic animals, any method known in the art for introducing a recombinant construct or transgene into an embryo or embryonic stem cell, such as microinjection, cell gun, transfection, liposome fusion, electroporation, and the like, may be used.

Many techniques can be used to introduce DNA into an egg or other nucleated cell, including in vitro fertilization using sperm as a carrier of exogenous DNA ("sperm mediated gene transfer", e.g., Lavitrano et al., 1989, Cell 57: 717–723), microinjection, gene targeting (Thompson et al., 1989, Cell 56: 313–321), electroporation (Lo, 1983, Mol. Cell. Biol. 3: 1803–1814), transfection, or retrovirus mediated gene transfer (Van der Putten et al., 1985, Proc. Natl. Acad. Sci. USA 82: 6148–6152). For a review of such techniques, see Gordon (1989), Transgenic Animals, Intl. Rev. Cytol. 115:171–229. Except for sperm-mediated gene transfer, eggs should be fertilized in conjunction with (before, during or after) other transgene transfer techniques. A preferred method for fertilizing eggs is by breeding the female with a fertile male. However, eggs can also be fertilized by in vitro fertilization techniques. The transgene containing nucleic acid encoding CD200 is preferably introduced during embryogenesis. The term embryogenesis means early phase of ontogeny in multi-cellular animals. The introduction of a nucleic acid sequence containing CD200 at the fertilized oocyte stage ensures that the introduced gene will be present in all cells of the transgenic animal. The presence of the introduced gene in all cells of the transgenic "founder" animal in turn means that all of the founder animal's offspring will carry the introduced gene in all of their cells.

In one embodiment, the transgenic animal is small laboratory animal including, but not limited to, a mouse, hamster, guinea pig, rat or rabbit. Transgenic rodents and rabbits and other small animals can be prepared using techniques known in the art. In one example, the transgene containing CD200 is introduced into an embryonic stem cell (ES) from the animal. ES cells are obtained from pre-implantation embryos cultured in vitro (Evans, M. J., et al., (1981) Nature 292, 154–156; Bradley, A., et al. (1984) Nature 309, 255–258; Grossler, et al., (1986) Proc. Natl. Acad. Sci. USA 83, 9065–9060; and Robertson, et al., (1986) Nature 322, 445–448). Transgenes can be efficiently introduced into ES cells by DNA transfection or by retrovirus-mediated transduction. The resulting transformed ES cells can thereafter be combined with blastocysts from a non-human animal. The ES cells colonize the embryo and contribute to the germ line of the resulting chimeric animal (For review see Jaenisch, R. (1988) Science 240, 1468–1474). Embryonic stem cells are useful as they can integrate into and become part of the germline of the developing embryo so as to create germline transmission of the nucleic acid construct or vector carrying the CD200 gene. Any embryonic stem cell that can integrate into the developing embryo may be used in the present invention. The embryonic stem cell is generally of the same species as the animal to be prepared i.e., to make a transgenic mouse, mouse embryonic stem cells are used. In one embodiment, the embryonic stem cell are isolated from mouse blastocysts, in particular from the 129/SvJ strain. The cells can be cultured prior to transfection with the nucleic acid construct or vector using methods well known in the art including the methods taught by Robinson in Teratocarcinomas and Embryonic Stem Cells: A Practical Approach, E. J. Robinson editor, IRL Press, Washington, D.C., 1987.

The vector can be inserted into the cells using techniques known in the art including electroporation, microinjection, viral infection and calcium phosphate treatment. Preferably, the vector is inserted using electroporation. Prior to insertion, the vector is first linearized using a suitable restriction enzyme that cuts within the vector sequence and not within the nucleic acid sequence containing the CD200 gene. After insertion into the cells the nucleic acid construct integrates with the genomic DNA of the cell. After transfection, the cells are cultured under conditions to detect transfected cells.

The embryonic stem cells are inserted to an early embryo for example using microinjection. For microinjection, approximately 10–20 embryonic stem cells are collected into a micropipette and injected into 3–5 day old blastocysts, preferably 3½ day old blastocysts, recovered from female animals. The injected blastocysts are re implanted into a pseudopregnant foster mother. Pseudopregnant animals can be obtained, for example, by placing 40–80 day old female animals, which are more than 8 weeks of age, in cages with infertile males, e.g., vasectomized males. The next morning females are checked for vaginal plugs. Females who have mated with vasectomized males are held aside until the time of transfer. The foster mother gives birth to pups, typically 20–21 days later, and the pups are screened for the presence of the nucleic acid construct of the invention. For example, the tail tissue of the pups may be screened using Southern blots and/or PCR. The heterozygotes are identified and can then be crossed with each other to generate homozygous animals.

In a preferred embodiment, the method of preparing the non-human animal with increased expression of a CD200 gene comprises: (a) obtaining a nucleic acid sequence containing an CD200 gene or portion thereof; (b) preparing a nucleic acid construct comprising the nucleic acid sequence containing the CD200 gene; (c) inserting the nucleic acid construct into an embryonic stem cell; (d) selecting a cell that has integrated the nucleic construct into its genome; (e) injecting said cell into a blastocyst to form a chimeric blastocyst; (f) implanting said chimeric blastocyst into a pseudopregnant mother wherein said mother gives birth to a transgenic animal containing the chimeric construct in its germline; and (g) breeding said transgenic animal to generate heterozygous animal that is heterozygous for the nucleic acid construct; and (h) optionally, mating together a male and female animal each heterozygous for the nucleic acid construct and selecting progeny that are homozygous for the nucleic acid construct.

In another example, the transgene containing CD200 is introduced into a developing embryo from the animal. The developing non-human embryo can be cultured in vitro to the blastocyst stage. During this time, blastomeres may be targets for retroviral infection (Jaenich, R. (1976) Proc. Natl. Acad. Sci. USA 73, 1260–1264). Efficient infection of the blastomeres is obtained by enzymatic treatment to remove the zona pellucida (Hogan et al., (1986) in Manipulating the Mouse Embryo, Cold Spring Harbor Laboratory Press, Cold Spring Harbor, N.Y.). The viral vector system used to introduce the transgene is typically a replication-defection retrovirus carrying the transgene (Jahner et al., (1985) Proc. Natl. Acad. Sci. USA 82, 6927–6931; Van der Putten et al., (1985) Proc. Natl. Acad. Sci. USA 82, 6148–6152). Transfection is easily and efficiently obtained by culturing the blastomeres on a monolayer of virus-producing cells (Van der Putten et al., (1985) Proc. Natl. Acad. Sci. USA 82, 6148–6152; Stewart et al., (1987) EMBO J. 6:383–388). Alternatively, infection can be performed at a later stage. Virus or virus-producing cells can be injected into the blastocoele (Jahner et al., (1982) Nature 298:623–628.) Most of the founder animals will be mosaic for the transgene since incorporation occurs only in a subset of the cells which formed the transgene non-human animal. Furthermore, the founder animal may contain retroviral insertions of the transgene at a variety of positions in the genome; these generally segregate in the offspring. In addition, it is also possible to introduce transgenes into the germ line, albeit with low efficiency, by intrauterine retoviral infection of the midgestation embryo (Jahner et al., (1982) Nature 298: 623–628).

The present invention also includes the preparation of larger animals including farm animals such as pigs, goats, sheep, horses and the like. In such a case the transgene is microinjected into pro-nuclei or nuclei of one cell or two cell embryos to make transgene mammals is widely practiced by those of skill in the art. As an example, transgene swine are routinely produced by the microinjection of a transgene transcription unit into pig zygotes or embryos. (See, for example, PCT Publication No. WO92/11757; Martin et al., "Production of transgene Swine" pp 315–388 in transgene Animal Technology: A Laboratory Handbook, Carl A Pinkert, ed., Academic Press (1994).)

Embryos of large mammals that have opaque embryos (e.g., pigs) are typically centrifuged to allow the visualization of the blastomere nuclei. Embryos are removed from the centrifuge tube and placed into a small dish for examination. If the cytoplasm is still opaque with lipid such that the nuclei are not sufficiently visible to allow visual verification of nuclear injection, the embryos may be centrifuged again.

Methods of microinjecting cells, such as zygotes and embryos, are well known in the art, and are described, for example, in Brinster, R. L. et al., Proc. Natl. Acad. Sci. USA 82:4438–4442 (1985). Such methods are also applicable to the microinjection of blastomere nuclei.

For microinjection, embryos can be placed on a suitable surface, in culture medium. Typically a drop of medium is used. Suitable media for the microinjection procedure in multicellular pre-gastrulation embryos are, for instance, modified BMOC-2 containing HEPES salts, as described in Ebert, K. M. et al. J. Embryol. Exp. Morph. 84:91–103 (1984); or PBS medium supplemented with 20% fetal calf serum (Jura, J. et al. Theriogenology 41:12S9–1266 (1994)) or Brinster's medium plus 25 .mu.M HEPES buffer (pH 7.4) (Brinster, R. L. et al. Proc. Natl. Acad. Sci. USA 82:4438–4442 (1985)). Of these, the first is most preferred. If desired, silicone oil or the like may be used to cover the drop of medium and to fill the lid to prevent the medium from evaporating.

An embryo to be injected is typically held in place by suction on a blunt holding pipet of a suitable diameter. Blastomere nuclei are then injected with a solution of isolated nucleic acid molecules via a sharp-tipped injector pipet. Swelling of the nucleus can generally be observed upon successful injection. The movements of the means for holding and injecting the cells are preferably controlled by appropriate micromanipulation instruments.

The process is best observed under a microscope using suitable magnification. Clones of isolated CD200 nucleic acid molecules can be injected into blastomere nuclei in a volume of 1–2 pl, optimally. More or less volume may be injected if desired, up to a maximum volume that does not cause irreparable damage to the nucleus or to the cell. Concentrations of the transgene clone may vary.

Embryos surviving the microinjection process, as judged, e.g., by microscopic observation of morphology, are preferably transferred to the reproductive tract of a recipient female shortly after introduction of the isolated nucleic acid molecules. In some instances it may be desirable for the surviving embryos to be cultured for a time and subsequently transferred. Surviving embryos are typically introduced into the oviduct or uterus, as appropriate so as to best match the developmental stage of the cultured embryo to the stage of pregnancy (or, although generally less preferred, pseudopregnancy) of the host female and the location of embryos in the reproductive tract of an animal at the corresponding stage of pregnancy). In some cases it may be more efficient to use donor females as recipients as well; i.e., subsequent to embryo collection, but while the animal is still undergoing the surgical procedure for embryo harvest, genetically altered embryos are introduced into the reproductive tract of the donor female, so as to utilize the donor as a recipient. See, for example, Pursel et al., Thieriogenology, 46:201–209 (1996).

When required or desired, in vitro incubation for some period of time before transferring the embryo into an appropriate female host animal is preferably carried out with as little delay as possible. Preferably the delay is no more than 5 hours, more preferably the delay is no more than 4 hours, even more preferably the delay is no more than 3 hours, most preferably the delay is no more than 2 hours.

The host animal that serves as a surrogate mother can be any animal that can provide the appropriate hormonal and nutritional environment for the growth and development of the embryo to term. Such an animal can be a pregnant female with embryos at or close to the same stage of development as the surviving embryo or embryos to be transferred to her reproductive tract, or an animal at a stage in the estrous cycle in which the reproductive tract would be receptive to the introduction of an early embryo. For example, the estrous cycle of pigs can be hormonally synchronized using norgestomet implants or by other means known as the art.

Preferably, the surrogate mother mammal is of the same species as the embryo. Usually, this is required for the development of the embryo to term. However, some exceptions are known. For example, one species of antelope can in some cases serve as surrogate mother for gestation of an embryo of a different species of antelope (Dresser, B. L. et al., Proc. Am. Assoc. Zool. Parks Aquar. 166–8 (1994)).

The present invention also provides a method of preparing a transgenic non-human animal containing a transgene comprising a nucleic acid sequence encoding CD200 comprising:

(a) providing a transgene comprising a nucleic acid sequence encoding CD200;

(b) introducing the transgene into a non-human embryonic cell;

(c) permitting said embryonic cell to develop into a non-transgenic human animal; and (d) identifying transgenic non human animals that express CD200.

The transgene preferably contains an inducible response element. In one embodiment, the inducible response element is a tetracycline response element that is inducible by providing doxycycline to the animal.

The transgenic non-human animal is preferably a rodent such as a mouse or rat.

III. Uses of the Transgenic Animal

The present invention includes any and all uses of the CD200 transgenic animals of the invention. In one embodiment, the transgenic animals are useful models in studying transplant rejection, fetal loss, allergy, autoimmune disease and cancer. The animals can assist in studying the role of CD200 in these diseases. As shown in Example 1, transgenic CD200 animals show prolonged survival of skin grafts as compared to control animals. The animals can also act as recipients for organ and bone marrow grafts. In another embodiment, the animals can be used to study myeloid differentiation and regulation. In a further embodiment, the animals can be used to study bone physiology and development.

In another embodiment, the transgenic animals of the invention are useful as animal models for testing potential agents that can modulate the effect of overexpression of CD200 and treat conditions involving CD200 overexpression. Over expression of CD200 is useful in treating or preventing transplantation rejection, fetal loss or autoimmune disease while reducing expression of CD200 is useful in treating cancer. Therefore, finding agents that can antagonize increased CD200 expression can be used as a cancer therapy.

Accordingly, the present invention provides a method to screen for agents that modulate the effect of CD200 expression comprising:

(a) administering a test agent to a transgenic non-human animal containing a transgene comprising a nucleic acid sequence encoding CD200; and (b) determining the effect of the test agent on functional effects of the expression of CD200.

The expression of the transgene is preferably inducible and the expression of CD200 is preferably induced prior to administering the test agent. The levels of CD200 expression can be compared to a control animal such as a transgenic CD200 animal not receiving the test agent, and the functional effects of putative CD200 agonists/antagonists are studied following CD200 induction.

The animals can also be used as disease models to test agents that can treat graft rejection, autoimmune disease, fetal loss and cancer. For example, a CD200 transgenic animal can be used to find potential agonists or antagonists of CD200 expression under certain disease states. Agonists are useful in treating diseases where it is desirable to induce CD200 expression such as transplantation, autoimmune disease and fetal loss. Antagonists are useful in treating diseases where it is desirable to reduce or inhibit CD200 expression such as cancer or infections by virus, bacteria, parasites and other pathogens. Potential agents can be tested on the animal and the effects on the disease model, as compared to CD200 transgenic animals not receiving the agent, can be assessed. The term "disease" means any condition or abnormal state that is not normally seen in a healthy animal such as autoimmune disease, animals receiving transplants, fetal loss syndromes and cancer.

Accordingly, the present invention provides a method for identifying a potential therapeutic agent for treating a disease comprising:

(a) providing a transgenic animal of the invention;
(b) introducing a disease to the animal;
(c) administering the potential agent to the animal; and
(d) determining the effect of the agent on the disease.

As an example, a CD200 transgenic animal can be used as a tumor recipient and CD200 can be induced. Potential agents that can reduce tumor growth/survival can be tested on the animal to test for an increase in survival (decreased tumor growth) as compared to CD200 transgenic animals receiving the tumor but not receiving the agent.

Accordingly, the present invention provides a method for identifying a potential therapeutic agent for prolonging survival in a tumor bearing animal comprising:

(a) providing a transgenic animal of the invention;
(b) introducing a tumor to the animal;
(c) administering the potential agent to the animal; and
(d) determining the effect of the agent on the survival of the animal.

In another embodiment, the present invention provides a method for identifying a potential therapeutic agent for reducing tumor growth in a tumor bearing animal comprising:

(a) providing a transgenic animal of the invention;
(b) introducing a tumor to the animal;
(c) administering the potential agent to the animal; and
(d) determining the effect of the agent on the growth of the tumor.

As a further example, a CD200 transgenic animal can be used as a skin graft recipient and CD200 can be induced. Potential agents or agonists that can prolong graft survival can be tested on the animal to look for an increase in graft survival as compared to CD200 transgenic animals not receiving the agent. Both the test and control animal would receive a transplant.

Accordingly, the present invention provides a method for identifying a potential therapeutic agent for prolonging transplant survival comprising:

(a) providing a transgenic animal of the invention;
(b) introducing a transplant to the animal;
(c) administering the potential agent to the animal; and
(d) determining the effect of the agent on transplant survival.

In the above disease models the transgenic animal preferably has inducible expression of the transgene and the CD200 is preferably included prior to the administration of the transplant, tumor or the test agent. A similar assay can be used for autoimmune disease and other diseases.

Antagonists of CD200 expression may also be an effective adjunctive strategy for vaccination in infectious disease (e.g. TB, AIDS, SARS etc.) In a test of such a strategy, transgenic mice would be induced of overexpress CD200, and vaccinated (against)/infected (with) the appropriate agent, in the presence/absence of suitable CD200 agonists/antagonists. A CD200 antagonist would be predicted to increase vaccine efficacy. In a reverse case, CD200 agonists would be predicted to stabilize/augment the protective effect of CD200 overexpression in transplantation, autoimmunity, and allergy (vide supra).

The above screening methods of the invention can advantageously also use cells isolated from a homozygous or heterozygous CD200 mutant non-human mammal, for example, immune cells including T-cells, isolated from a CD200 mutant non-human of the invention for a desired purpose.

The test agents in the screening assays can be generated by methods well known to those skilled in the art, for example, well known methods for producing pluralities of compounds, including chemical or biological molecules such as simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., Curr. Opin. Chem. Biol. 2:422–428 (1998); Tietze et al., Curr. Biol., 2:363–371 (1998); Sofia, Mol. Divers. 3:75–94 (1998); Eichler et al., Med. Res. Rev. 15:481–496 (1995); and the like. Libraries containing large numbers of natural and synthetic compounds, including antibodies, also can be obtained from commercial sources. Combinatorial libraries of molecules can be prepared using well known combinatorial chemistry methods (Gordon et al., J. Med. Chem. 37: 1233–1251 (1994); Gordon et al., J. Med. Chem. 37: 1385–1401 (1994); Gordon et al., Acc. Chem. Res. 29:144–154 (1996); Wilson and Czarnik, eds., Combinatorial Chemistry: Synthesis and Application, John Wiley & Sons, New York (1997)).

The following non-limiting examples are illustrative of the present invention:

EXAMPLES

Example 1

Materials and Methods

Mice

Male C57BL/6 mice, along with NMRI breeder mice carrying a reverse tetracycline regulated transactivator gene (TgN(rtTAhCMV)4Uh-abbreviated hereafter as rtTA$^{tg}$), were purchased from the Jackson laboratories, Bar Harbour, Me. Mice were housed 5/cage and allowed food and water ad libitum. All mice were used at 8–12 weeks of age. Genotyping of progeny from further backcrosses of rtTA$^{tg}$ to C57BL/6 mice used primer pairs designed in accordance with the Jackson laboratories instructions (see below and FIG. 1a).

The Primer Pairs Used for Characterization of These Mice Were as Follows:

Control primer pairs for tTA transgene; amplifies 200 bp fragment from wild-type allele

```
Tcrd primer
5'CAAATGTTGCTTGTCTGGTG3'      (SEQ ID NO.:1)

Tcrd antisense primer
5'GTCAGTCGAGTGCACAGTTT3'      (SEQ ID NO.:2)
```

Primer pairs for tTA transgene; amplifies 450 bp fragment from the tTA portion of transgene

```
Tet sense primer:
5'CGCTGTGGGGCATTTTACTTTAG3'   (SEQ ID NO.:3)

Tet antisense primer:
5'CATGTCCAGATCGAAATCGTC3'     (SEQ ID NO.:4)
```

Creation of TRE-CD200-GFP cDNA, and Characterization of Transgenic Mice:

cDNA encoding green fluorescent protein (GFP) was cut from pEGFP-N2 (Clonetech) and linked in frame immediately downstream of a tetracycline response element (TRE) gene, and verified by sequencing from a PTRE2 vector using primer pairs (5'-ACATGAATTTTACAATAGCG-3') (SEQ ID NO.: 5) and GFP primer (5'-AACCGTCAGATCGC-CTGGAG-3') (SEQ ID NO.: 6), flanking the cloning sites in the vector. Sequences were analyzed using the DNAsis for windows, sequence analysis software (Hitachi Software Engineering America Ltd, USA). The CD200 gene was ligated into this TRE-GFP construct using SacII and BamH1 sites. Confirmation of in-frame ligation of TRE-CD200-GFP was made by sequencing using the same primer pairs as described above.

In preliminary studies (not shown) the inventor confirmed that co-transfection of CHO cells with both the TRE-CD200-GFP cDNA and rtTAhCMV cDNA led to a doxycycline inducible increase in both GFP (assessed by fluorescence) and CD200 (as determined by western analysis of extracts of transfected, doxycycline-induced cells, analysed using a previously described anti-CD200 mAb[24]). Moreover, using CHO cells transfected with this TRE-CD200-GFP construct and stimulated with doxycyline we verified that surface detection by the anti-CD200 mAb was still apparent, and that the transfected CHO cells caused inhibition of MRL reactivity, as previously described for CHO cells transfected with CD200 alone (see [25]).

Purified TRE-CD200-GFP cDNA was used to transfect embryonic stem cells (University Health Network Transgenic facility), the embryos transferred to pseudopregnant foster mothers, and subsequent progeny typed for wild-type and transgenic CD200 using the same forward primer (from the V-region exon of CD200) and 3' primer pairs to distinguish the endogenous germline CD200 and the transgenic CD200-GFP genes as follows.

Sense primer for both endogenous and transgenic CD200 (from V-region exon 3):

5'-GMGTGGTGACCCAGGATGA-3' (SEQ ID NO.: 7)

Antisense primer for endogenous CD200 (from 5' end of the intron immediately downstream of exon 3)

5'-TGCTGGCTGTACCCTTAGAA-3' (SEQ ID NO.: 8)

Antisense primer for transgenic CD200-GFP (from 3' end of GFP cDNA)

5'-TCGTGCTGCTTCATGTGGTC-3' (SEQ ID NO.: 9)

Of 25 progeny screened (9 males and 16 females) positive transmission of CD200-GFP was detected in 15 (4 males and 11 females), and germline transmission in 6 (2 males and 4 females). Typical PCR data showing detection of germline and transgenic CD200 in representative mice are shown in FIG. 1b. First generation transgenic progeny were backcrossed onto a C57BL/6 (H2b/b) background, typed at each generation, and 3 founder lines of each continued through further backcross generations with C57BL/6. At the 6th. backcross transgenic (F6) mice were crossed with rtTAh-CMV transgenic mice, offspring typed for both rtTA and CD200-GFP transgenes, and positive progeny (referred to subsequently as F16s) used in the transplantation model described below. Some mice were used at earlier (n) backcross generations (F1n) following mating with rtTAhCMV transgenic mice for in vitro studies.

Figure 2:
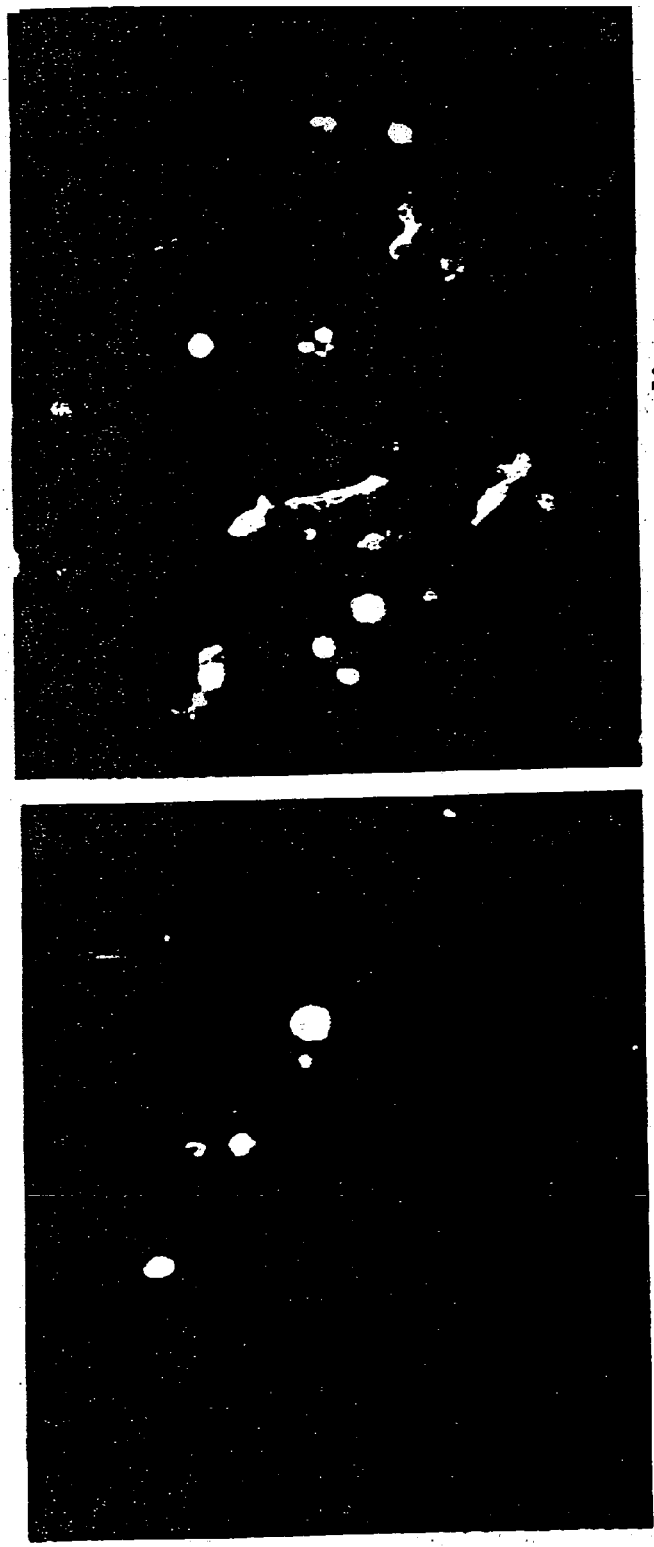
FIG. 2 illustrates induction of GFP expression in fibroblasts (tail skin) prepared from $F1_2$ cross of rtTA$^{tg}$ and TRE-CD200-GFP$^{tg}$ mice, after incubation of fibroblasts in the presence (panel b) or absence of doxyxcyline (panel a).

Doxycycline Induction of GFP and CD200 Expression in F1n Mice:

Peripheral blood cells (PBL) were obtained in heparinized tubes from the tail of doubly transgenic F1n mice (~100 ml of blood/donor), before and after allowing mice to drink plain water or water with 2 mg/ml doxycycline hydrochloride (Sigma Chemicals, St.Louis, Mo.) with 5% sucrose (Dox-water) for a minimum of 3 days-fresh water or Dox-water was used at 3 day intervals. Pre- and post-induction PBL were spun over mouse lymphopaque (Cedarlane Laboratories, Hornby, Ontario, Canada) and examined by FACS for fluorescence (GFP). In addition an aliquot of cells was incubated with FITC-labeled anti-CD200 and again examined by FACS. Animals typed as CD200-inducible were used as cell/organ donors, for immunization in vitro, and skin graft studies in vivo(F16). At sacrifice cells obtained from various tissues of these Dox-water treated mice were also analysed by FACS for expression of GFP and CD200. Data in FIG. 2 show GFP expression in fibroblasts obtained from F12 mice, cultured in the presence/absence of doxycyline.

Monoclonal Antibodies:

The following monoclonal antibodies (mAbs) were obtained from Pharmingen (San Diego, Calif., USA) unless stated otherwise: anti-IL-2 (S4B6, ATCC; biotinylated JES6-5H4); anti-IL-4 (11B11, ATCC; biotinylated BVD6-24G2); anti-IFNg (R4-6A2, ATCC; biotinylated XMG1.2); anti-IL-10 (JES5-2A5; biotinylated, SXC-1); anti-IL-6 (MP5-20F3; biotinylated MP5-32C11); anti-TNFa (G281-2626; biotinylated MP6-XT3); FITC anti-CD80, FITC anti-CD86, FITC anti-CD40, FITC anti-abTCR, L3T4 (anti-mouse CD4), anti-thy1.2 and anti-Ly2.2 were obtained from Cedarlane Labs, Hornby, Ontario. The hybridoma producing DEC205 (anti-mouse dendritic cells) was a kind gift from Dr. R. Steinman, and was directly labeled with FITC; unconjugated and FITC-conjugated rat anti-mouse CD200 was obtained from BioCan Inc., Mississauga, Ontario, Canada. The rat anti-mouse CD200R used was characterized elsewhere[24].

Strepavidin horse radish peroxidase and recombinant mouse GM-CSF was purchased from Pharmingen (San Diego, Calif.).

Preparation of Cells:

Single cell suspensions from different tissues were prepared aseptically by incubation of teased tissue in collagenase for 30 minutes at 37° C., and after centrifugation cells were resuspended in a-Minimal Essential Medium supplemented with 2-mercaptoethanol and 10% fetal calf serum (aF10). LPS splenic DC, stained (>90%) with DEC205, were obtained by overnight culture (1 mg/ml LPS) of adherent fresh spleen cells.

Skin Allotransplantation Using Tissue From CD200-Transgenic Mice:

All procedures were performed as described earlier. Allogeneic skin grafts were obtained from individual female donors of C57BL/6 origin, or doubly transgenic (rtTA$^{tg}$ and TRE-CD200-GFP$^{tg}$) and non-transgenic F16 mice, and grafted to 4/group adult (8-week) C3H mice. All animals received Dox-water for the drinking supply. Mice were sacrificed at 14 days, spleen cells harvested, and assayed at different E:T ratios for lysis of EL4 or P815 target cells.

Cytotoxicity and Cytokine Assays:

In allogeneic mouse mixed leukocyte cultures (MLC) used to assess cytokine production, F1n responder cells were stimulated with equal numbers of mitomycin-C treated (45 min at 37° C.) BALB/c spleen stimulator cells in triplicate in aF10. Supernatants were pooled at 40 hr from replicate wells and assayed in triplicate in ELISA assays for lymphokine production with capture and biotinylated detection mAbs as described above. Varying volumes of supernatant were bound in triplicate at 4° C. to plates pre-coated with 100 ng/ml mAb, washed ×3, and biotinylated detection antibody added. After washing, plates were incubated with strepavidin-horse radish peroxidase (Cedarlane Labs), developed with appropriate substrate and OD405 determined using an ELISA plate reader. Recombinant cytokines for standardization were obtained from Pharmingen (U.S.A.). All assays showed sensitivity in the range 40 to 4000 pg/ml.

Where cytotoxicity was assayed, cells were harvested from MLR cultures at 5 days and titrated at different effector:target ratios for killing (4 hrs at 37° C.) of $^{51}$Cr-labeled P815 tumor target cells.

Results

Figure 3:
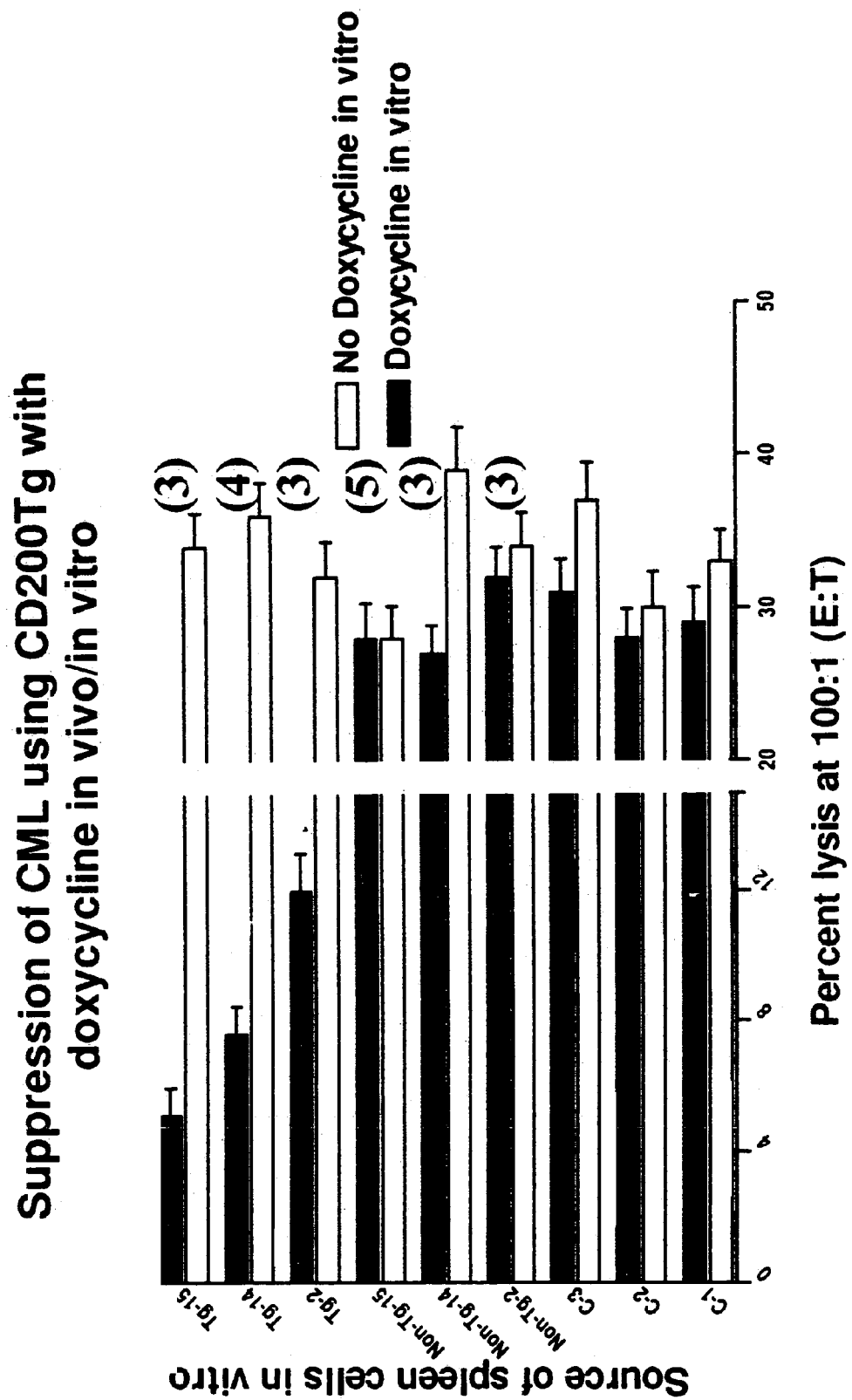
FIG. 3 illustrates inhibition of induction of CTL following allostimulation of spleen cells from doubly transgenic (rt-TA$^{tg}$ and TRE-CD200-GFP$^{tg}$) $F1_6$ mice in the presence of doxycycline. MLR cultures were initiated using BALB/c spleen stimulator cells, and individual responder spleen cells from three different founder lines, after typing PBL from those spleen donors for expression of TRE-CD200-GFP in the simultaneous presence/absence of the rtTA[tg]. The number of donors used from each founder line is shown in parentheses. CTL assays were performed using $^{51}$Cr P815 target cells at day 5 of culture. Data show arithmetic mean (±SD) specific lysis for the different groups at an effector:target ratio of 100:1.
Figure 4:
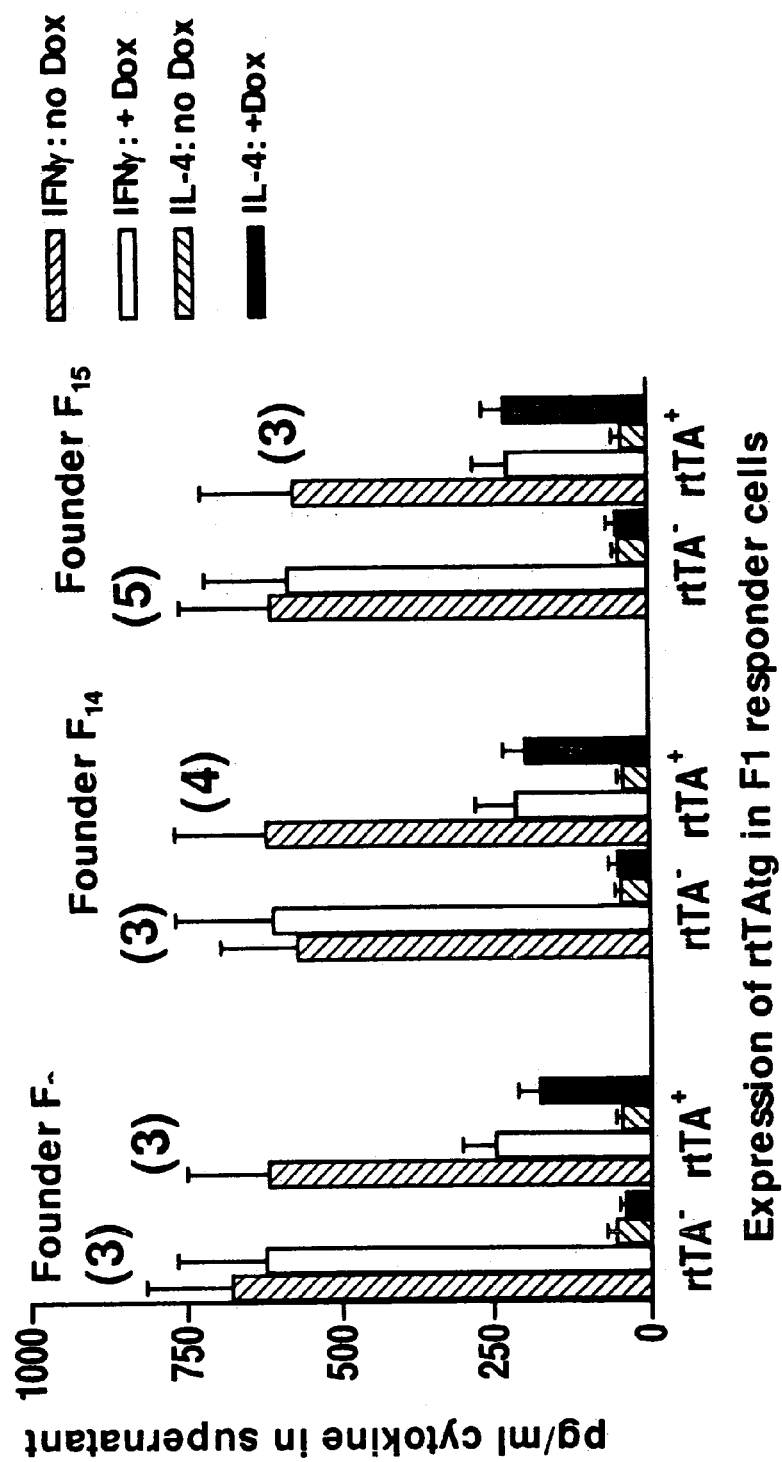
FIG. 4 illustrates altered induction of cytokine production (increased IL-4, decreased IFNγ) measured by ELISA in 40 hr cultures of cells from mice shown in FIG. 3. Data show arithmetic mean (±SD) cytokine concentration (pg/ml) for the different groups. Qualitatively equivalent patterns (to IFNγ, IL-4) were seen for IL-2 and IL-10 respectively (data not shown for clarity).

Suppression of Induction of CTL and Type-1 Cytokines From Spleen Cells of Transgenic Mice Stimulated with Alloantigen in the Presence of Doxycycline:

PBL samples from F16 mice of (rtTAtg×TRE-CD200-GFPtg) matings (each Tg mouse parent was at the 6th. generation of backcross to C57BL/6; F16 mice derived from 3 founder lines of TRE-CD200-GFP were used) were typed for expression of the independent transgenes using the primer pairs described. Spleen cell preparations were prepared from individual doubly transgenic mice and single-transgenic mice (referred to as non-tg), and cultured in the presence/absence of doxycycline with mitomycin-c treated BALB/c spleen stimulator cells. Cytokines were assayed in supernatants at 40 hrs by ELISA, and CTL directed to P815 tumor targets at day 5 of culture. Data in FIGS. 3 and 4 show CTL responses and cytokine profiles respectively under these conditions.

It is clear from these data that while exposure to doxycycline per se has no significant effect on induction of CTL of IFNg production in cells obtained from singly transgenic TRE-CD200-GFP mice (no rtTAtg, so no induction of CD200 by doxycycline-see FIG. 2), in contrast, doxycycline caused profound alterations in MLR responses of cells from all 3 founder lines of doubly transgenic mice. In all cases there was inhibition of CTL induction (FIG. 3) and decreased IFNg production, with increased IL-4 (see FIG. 4), though the degree of suppression (of CTL, or of IFNg production) was somewhat variable. A similar suppression of CTL and type-1 cytokine production was observed in earlier reports following infusion of a solubilized form of CD200 (CD200Fc)[27], or following in vivo induction of CD200 expression in mice following portal vein alloimmunization[28].

Figure 5:
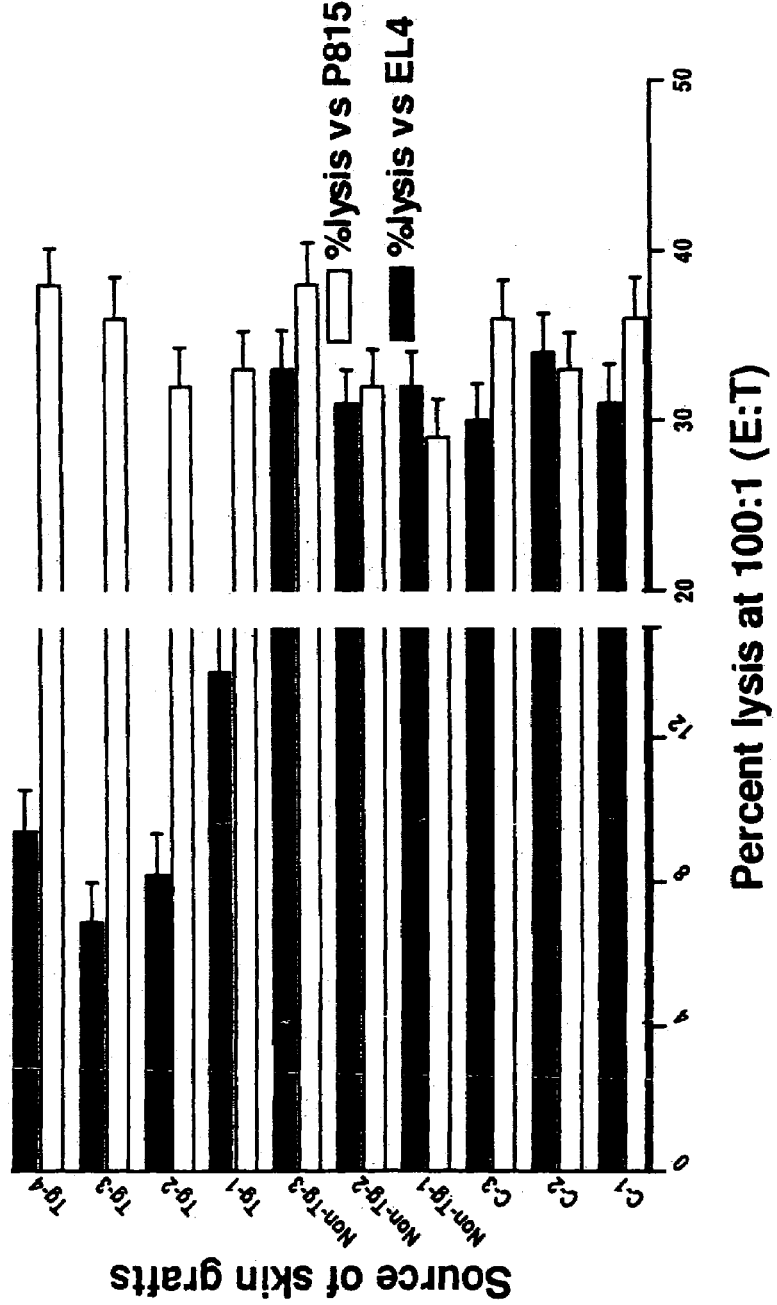
FIG. 5 illustrates the inhibition of induction of CTL in vivo following engraftment of 4/group C3H mice with tail skin from 4 doubly transgenic (rtTA[tg] and TRE-CD200-GFP[tg]) F1$_6$ mice in the presence of doxycycline. Tail skin from 3 each Non-tg or control (stock C57BL/6) donors were used in control groups. All doubly-transgenic mice used were from founder 14 (see FIGS. 3/4). Control skin grafts (from stock BALB/c mice) were applied to the opposite flank of all recipients. All mice were sacrificed at 14 days post grafting. Data shown are mean % lysis (100:1 effector:target) (±SD) using spleen cells from each group of recipients (4 mice/original tail skin donor).

Suppression of Induction of CTL In Vivo Following Skin Allografting Using Tail Skin From Doubly-Transgenic Mice:

In order to assess the effect of CD200-transgene expression on allosensitization and graft survival in vivo, the inventor performed the following studies. Doubly-transgenic mice (and Non-tg littermate controls) received doxycycline in their drinking supply for a total of 8 days. Mice were sacrificed, various tissues snap-frozen in liquid nitrogen for phenotyping for transgenic CD200 expression (see Materials and Methods), and tail skin obtained from individual mice. 4 adult C3H recipients received 1 cm2 tail skin grafts from each individual donor, along with 1 cm2 tail skin grafts from BALB/s donors (third-party control) on the opposite flank. In studies using F1 doubly-transgenic mice from founder 14 and their controls (see FIGS. 3 and 4), all recipient mice received doxycycline in their drinking supply, and were sacrificed at 14 days. Spleen cell suspensions were prepared, and tested at different E:T ratios for lysis of EL4 or P815 (third-party control) target cells. These data (FIG. 5) showed unequivocally that in the presence of doxycycline, skin grafts from doubly-transgenic mice failed to sensitize to produce allospecific CTL (vs EL4 targets) as effectively as control skin grafts (stock BL/6 mice, or non-transgenic controls). All recipients were equally sensitized using BALB/c skin grafts. Additional phenotyping control studies (by PCR-not shown) confirmed CD200 transgene expression in the skin grafts used.

Figure 6:
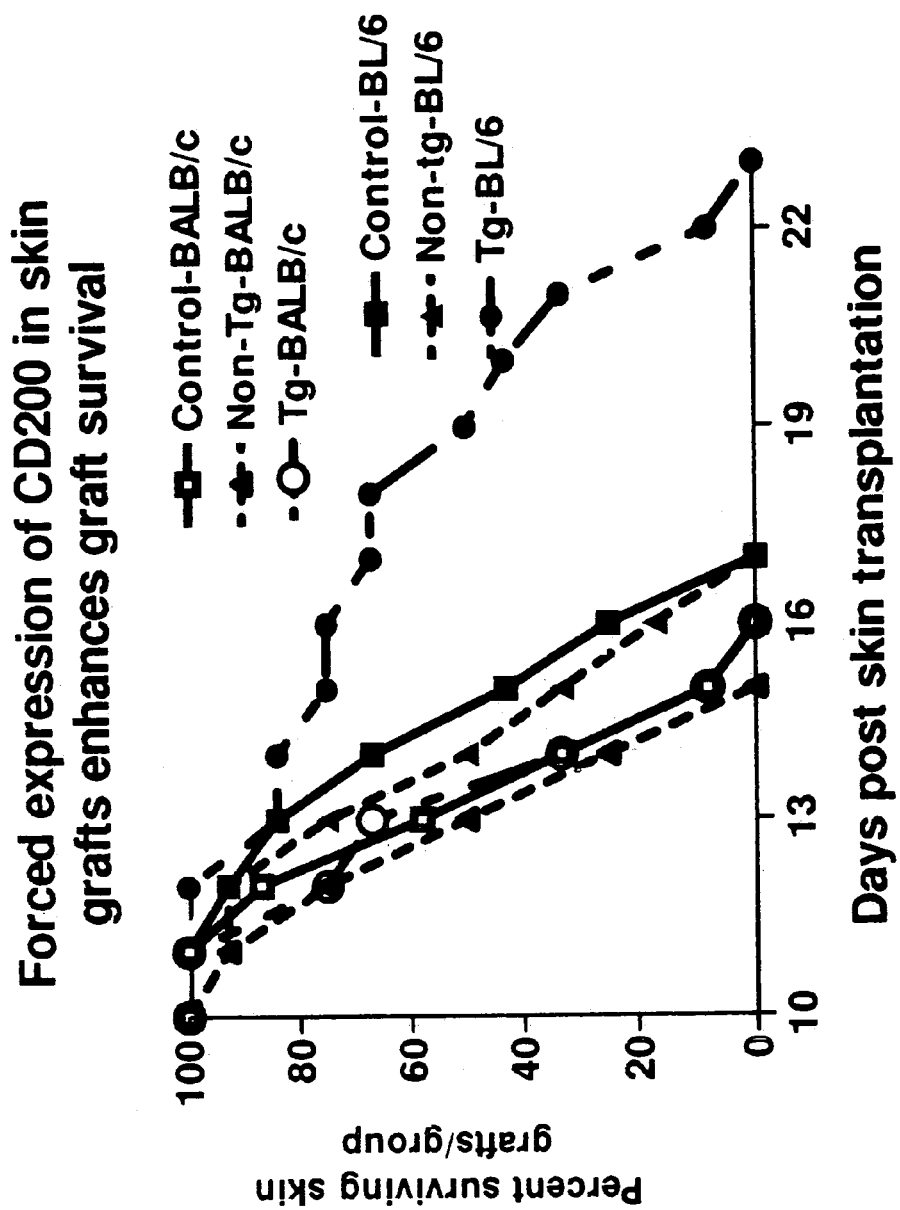
FIG. 6 illustrates the inhibition of induction of tail skin graft rejection following engraftment of 4/group C3H mice with tail skin from 3 doubly transgenic (rtTA[tg] and TRE-CD200-GFP[tg]) F1$_6$ mice in the presence of doxycycline. Tail skin from 3 each Non-tg and stock BL/6 donors were used in control groups. All doubly-transgenic and Non-tg control mice used were from founder 2 (see FIGS. 3/4). Control skin grafts (from stock BALB/c mice) were applied to the opposite flank of all recipients. Skin grafts in all mice were followed daily post grafting. Data shown are % surviving grafts for all groups.

In a final study, using as skin graft donors F1 mice from 6th. generation Founder 2 (see FIGS. 3 and 4), skin grafts were applied to 4 recipient C3H mice/tail donor as before, but in this case graft survival was monitored daily. In all cases recipient mice received doxycycline in their drinking supply, and a control (BALB/c) skin graft was again used for all recipients. Data in FIG. 6 are pooled from all 12 recipients used in the 3 groups (3 stock BL/6 donors; 3 Non-tg donors; 3 doubly-transgenic donors). Once again (not shown) PCR data confirmed CD200 expression in skin from doubly-transgenic mice.

It is apparent from these data, and consistent with data in previous Figures, that forced expression of CD200 in the doubly-transgenic offspring of Founders 2 produced antigen-specific enhanced skin graft survival in these mice.

Discussion

Previous studies from the inventor's laboratory have documented a role for increased expression of the molecule CD200 in immunosuppression in general[27], and in particular, in the suppression of rejection of allografts in vivo [28,29]. Moreover, preliminary evidence using a soluble form of CD200, CD200Fc, has suggested a role for CD200Fc in increasing xenograft survival[27]. In these studies, using cells from treated animals, increased graft survival was correlated with a polarization in cytokine production towards type-2 cytokines, and decreased induction of graft specific CTL. Based on these results the inventor has performed studies to investigate in detail the effect of transgenic expression of CD200 on alloimmunity and graft survival in mice.

Data presented in FIGS. 1 and 2 confirm that the doxycycline-inducible system the inventor has chosen does indeed lend itself to investigation of analysis of over-expression of CD200 in the presence of doxycycline in vivo and in vitro, using both GFP (fluorescence) and PCR typing analysis. Furthermore, and as is seen from FIGS. 3 and 4, the inventor was able to document in 3 independent founder lines, that forced expression of CD200 produced immunosuppression (of CTL induction) and altered polarization of cytokine production (decreased IFNg, increased IL-4) in a fashion we had predicted from the effects of soluble CD200Fc (or anti-CD200R) in MLC responses obtained from normal mice[28,29]. Most strikingly, when the inventor used as tail skin donors, grafts from mice over-expressing CD200, the inventor found that those grafts failed to induce allosensitization in vivo (FIG. 5), and showed increased survival (FIG. 6) when compared with grafts from Non-tg littermate controls.

In conclusion, the present data suggest that forced expression of CD200 can play an important role in achieving prolongation of graft survival in experimental animals. Graft prolongation is associated with decreased type-1 cytokine production, and loss of CTL induction.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

FULL CITATIONS FOR CERTAIN REFERENCES REFERRED TO IN THE SPECIFICATION

[1] Mackay, I. R. (2000) Brit Med J 321, 93–96.
[2] Fischbein, M. P., Ardehali, A., Yun, J., Schoenberger, S., Laks, H., Irie, Y., Dempsey, P., Cheng, G. H., Fishbein, M. C. and Bonavida, B. (2000) J Immunol 165, 7316–7322.
[3] Ozkaynak, E., Gao, W., Shemmeri, N., Wang, C. C., Gutierrez Ramos, J. C., Amaral, J., Qin, S. X., Rottman, J. B., Coyle, A. J. and Hancock, W. W. (2001) Nat Immunol 2, 591–596.
[4] Salomon, B. and Bluestone, J. A. (2001) Annu Rev Immunol 19, 225–252.
[5] Wang, S. D., Zhu, G. F., Chapoval, A. I., Dong, H. D., Tamada, K., Ni, J. and Chen, L. P. (2000) Blood 96, 2708–2713.
[6] Greenwald, R. J., Boussiotis, V. A., Lorsbach, R. B., Abbas, A. K. and Sharpe, A. H. (2001) Immunity 14, 145–155.
[7] Trambley, J., Bingaman, A. W., Lin, A., Elwood, E. T., Waitze, S. Y., Ha, J. W., Durham, M. M., Corbascio, M., Cowan, S. R., Pearson, T. C. and Larsen, C. P. (1999) J Clin Invest 104, 1715–1722.
[8] Trambley, J., Lin, A., Elwood, E., Bingaman, A. W., Lakkis, F., Corbascio, M., Pearson, T. C. and Larsen, C. P. (2001) Transplantation 71, 537–543.
[9] Yamada, A., Salama, A. D. and Sayegh, M. H. (2002) J Amer Soc Nephrol 13, 559–575.
[10] Harada, H., Ishikura, H., Nakagawa, I., Shindou, J., Murakami, M., Uede, T., Koyanagi, T. and Yoshiki, T. (2000) Urol Res 28, 69–74.
[11] Kishimoto, K., Dong, V. M., Issazadeh, S., Fedoseyeva, E. V., Waaga, A. M., Yamada, A., Sho, M., Benichou, G., Auchincloss, H., Grusby, M. J., Khoury, S. J. and Sayegh, M. H. (2000) J Clin Invest 106, 63–72.
[12] Najafian, N. and Sayegh, M. H. (2000) Expert Opin Investig Drugs 9, 2147–2157.
[13] Shevach, E. M., McHugh, R. S., Piccirillo, C. A. and Thornton, A. M. (2001) Immunol Rev 182, 58–67.
[14] Gorczynski, R. M. (2001) Eur J Immunol 31, 2331–2337.
[15] Lee, R. S., Rusche, J. R., Maloney, M. E., Sachs, D. H., Sayegh, M. H. and Madsen, J. C. (2001) J Immunol 166, 1572–1582.
[16] Linsley, P. S., Greene, J. L., Tan, P., Bradshaw, J., Ledbetter, J. A., Anasetti, C. and Damle, N. K. (1992) Journal of Experimental Medicine 176, 1595–1604.
[17] Gorczynski, R. M., Yu, K. and Clark, D. (2000) J Immunol 165, 4854–4860.
[18] Gorczynski, R. M., Chen, Z. Q., Yu, K. and Hu, J. (2001) Clin Immunol 101, 328–334.
[19] Gorczynski, R. M., Chen, Z., Lee, L., Yu, K. and Hua, J. (2002) Clin. Immunol. In press.
[20] Hoek, R. M., Ruuls, S. R., Murphy, C. A., Wright, G. J., Goddard, R., Zurawski, S. M., Blom, B., Homola, M. E., Streit, W. J., Brown, M. H., Barclay, A. N. and Sedgwick, J. D. (2000) Science 290, 1768–1771.
[21] Gorczynski, R. M. (2002) Mod. Asp. Immunobiol. In press.
[22] Gorczynski, R. M., Hu, J., Chen, Z., Kai, Y. and Lei, J. (2002) Transplantation in press.
[23] Harding, T. C., Geddes, B. J., Murphy, D., Knight, D. and Uney, J. B. (1998) Nature Biotech. 16, 553–555.
[24] Ragheb, R., Abrahams, S., Beecroft, R., Hu, J., Ni, J., Ramakrishna, V., Yu, G. and Gorczynski, R. M. (1999) Immunology Letters 68, 311–315.
[25] Gorczynski, R. M., Bransom, J., Cattral, M., Huang, X., Lei, J., Xiaorong, L., Min, W. P., Wan, Y. and Gauldie, J. (2000) Clin Immunol 95, 182–189.
[26] Gorczynski, R. M. (1995) Cell. Immunol. 160, 224–231.
[27] Gorczynski, R. M., Cattral, M. S., Chen, Z. G., Hu, J. A., Lei, J., Min, W. P., Yu, G. and Ni, J. (1999) J Immunol 163, 1654–1660.
[28] Gorczynski, R. M., Chen, Z., Fu, X. M. and Zeng, H. (1998) Transplantation 65, 1106–1114.
[29] Gorczynski, R. M., Chen, Z., Kai, Y. and Lei, J. (2000) Clin Immunol 97, 69–78.
[30] Barclay, A. N. (1981) Immunology 44, 727–36.
[31] Chen, Z., Zeng, H. and Gorczynski, R. M. (1997) Bba Mol Basis Dis 1362, 6–10.
[32] Wright, G. J., Puklavec, M. J., Hoek, R. M., Sedgewick, J. D., Brown, M. H. and Barclay, A. N. (2000) Immunity 13, 233–242.
[33] Wu, G. S., Korsgren, O., Zhang, J. G., Song, Z. S., vanRooijen, N. and Tibell, A. (2000) Xenotransplantation 7, 214–220.
[34] Benda, B., Lycke, N., Holstad, M. and Korsgren, O. (2000) Xenotransplantation 7, 206–213.

I claim:

1. A transgenic mouse whose somatic and germ line cells contain a transgene comprising a nucleic acid sequence encoding CD200 operably linked to a tetracycline inducible promoter wherein said transgenic mouse upon overexpression of said transgene exhibits inhibition of CTL induction, decreased IFNγ production and increased IL-4 production.

2. The transgenic mouse of claim 1 wherein the nucleic acid sequence is linked to a reporter gene.

3. The transgenic mouse according to claim 2 wherein the reporter gene encodes a green fluorescent protein.

4. The transgenic mouse of claim 1 wherein the nucleic acid encoding CD200 is murine.

5. A method of preparing a transgenic mouse according to claim 1 comprising the steps of
   (a) providing a transgene comprising a nucleic acid sequence encoding CD200 operably linked to a tetracycline inducible promoter;
   (b) introducing the transgene into a mouse embryonic cell;
   (c) permitting said embryonic cell to develop into a mouse; and
   (d) identifying transgenic mice that express CD200.

6. A method to screen for agents that modulate CD200 expression in mice comprising of the steps of (a) administering a test agent to the transgenic mouse of claim 1; and (b) determining the effect of the test agent on the expression of CD200 in said transgenic mouse.

7. A method for identifying a potential therapeutic agent for prolonging survival in a tumor bearing mouse comprising:
   (a) providing the transgenic mouse of claim 1;
   (b) introducing a tumor to the mouse;
   (c) administering the potential agent to the mouse; and
   (d) determining the effect of the agent on the survival of the mouse.

8. A method for identifying a potential therapeutic agent for reducing tumor growth in a tumor bearing mouse comprising:
   (a) providing the transgenic mouse of claim 1;
   (b) introducing a tumor to the mouse;
   (c) administering the potential agent to the mouse; and
   (d) determining the effect of the agent on the growth of the mouse.

9. A method for identifying a potential therapeutic agent for prolonging transplant survival in a mouse comprising:
   (a) providing the transgenic mouse of claim 1;
   (b) introducing a transplant to the mouse;
   (c) administering the potential agent to the mouse; and
   (d) determining the effect of the agent on transplant survival.

* * * * *

SEQUENCE LISTING

<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: Tcrd primer

<400> SEQUENCE: 1
caaatgttgc ttgtctggtg                                                    20

<210> SEQ ID NO 2
<211> LENGTH: 20
<212> TYPE: DNA
<213> ORGANISM: Artificial Sequence
<220> FEATURE:
<223> OTHER INFORMATION: Tcrd antisense primer

<400> SEQUENCE: 2
gtcagtcgag tgcacagttt                                                    20

<210> SEQ ID NO 3
<211> LENGTH: 23
<212> TYPE: DNA
<213> ORGANISM: Artificial Sequence
<220> FEATURE:
<223> OTHER INFORMATION: Tet sense primer

<400> SEQUENCE: 3
cgctgtgggg cattttactt tag                                                23

<210> SEQ ID NO 4
<211> LENGTH: 21
<212> TYPE: DNA
<213> ORGANISM: Artificial Sequence
<220> FEATURE:
<223> OTHER INFORMATION: Tet antisense primer

<400> SEQUENCE: 4
catgtccaga tcgaaatcgt c                                                  21

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
acatgaattt tacaatagcg                                                    20

<210> SEQ ID NO 6
<211> LENGTH: 20
<212> TYPE: DNA
<213> ORGANISM: Artificial Sequence
<220> FEATURE:
<223> OTHER INFORMATION: GFP primer

<400> SEQUENCE: 6
aaccgtcaga tcgcctggag                                                    20

<210> SEQ ID NO 7
<211> LENGTH: 20

```
<212> TYPE: DNA
<213> ORGANISM: Artificial Sequence
<220> FEATURE:
<223> OTHER INFORMATION: Sense primer for CD200

<400> SEQUENCE: 7
gaagtggtga cccaggatga                                               20

<210> SEQ ID NO 8
<211> LENGTH: 20
<212> TYPE: DNA
<213> ORGANISM: Artificial Sequence
<220> FEATURE:
<223> OTHER INFORMATION: Antisense primer for endogenous CD200

<400> SEQUENCE: 8
tgctggctgt acccttagaa                                               20

<210> SEQ ID NO 9
<211> LENGTH: 20
<212> TYPE: DNA
<213> ORGANISM: Artificial Sequence
<220> FEATURE:
<223> OTHER INFORMATION: Antisense primer for transgenic CD200-GFP

<400> SEQUENCE: 9
tcgtgctgct tcatgtggtc                                               20
```